(12) United States Patent
Foster et al.

(10) Patent No.: US 12,396,852 B2
(45) Date of Patent: Aug. 26, 2025

(54) MEDICAL DEVICE INCLUDING ATTACHABLE COMPONENTS

(71) Applicant: BOSTON SCIENTIFIC SCIMED, INC., Maple Grove, MN (US)

(72) Inventors: Daniel J. Foster, Lino Lakes, MN (US); Christopher Jay Scheff, Elk River, MN (US); Bradley S. Swehla, Eagan, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 769 days.

(21) Appl. No.: 17/583,481

(22) Filed: Jan. 25, 2022

(65) Prior Publication Data

US 2022/0233314 A1     Jul. 28, 2022

Related U.S. Application Data

(60) Provisional application No. 63/141,795, filed on Jan. 26, 2021.

(51) Int. Cl.
*A61F 2/24* (2006.01)
*A61F 2/95* (2013.01)
*A61M 25/01* (2006.01)

(52) U.S. Cl.
CPC ......... *A61F 2/2466* (2013.01); *A61F 2/2427* (2013.01); *A61F 2/243* (2013.01);
(Continued)

(58) Field of Classification Search
CPC ........ A61F 2/95; A61F 2/9522; A61F 2/2427; A61F 2/243; A61F 2/2433; A61F 2/2436;
(Continued)

(56) References Cited

U.S. PATENT DOCUMENTS 3,674,014 A   7/1972   Tillander
4,798,598 A   1/1989   Bonello et al.
(Continued)

FOREIGN PATENT DOCUMENTS

EP   0778040 A2   6/1997
EP   1168986 A1   1/2002
(Continued)

OTHER PUBLICATIONS

International Search Report and Written Opinion dated Mar. 2, 2018 for International Application No. PCT/US2017/062113.
(Continued)

*Primary Examiner* — William H Matthews
(74) *Attorney, Agent, or Firm* — Seager, Tufte & Wickhem LLP

(57) ABSTRACT

An example system for delivering an implantable heart valve is disclosed. The system includes a connection assembly including: an inner shaft having a proximal end region, a distal end region and a first coupling member disposed along a portion of the distal end region, wherein the first coupling member includes a plurality of apertures. The connection assembly also includes a support shaft and a second coupling member, wherein the second coupling member includes a stem, wherein the stem includes a groove extending circumferentially around the stem. The connection assembly also includes a plurality of bearings, wherein a portion of each bearing is disposed in a portion of the groove. The connection assembly also includes a locking cap coupled to the inner shaft, wherein a portion of the locking cap is configured to cover at least a portion of each of the plurality of bearings.

20 Claims, 9 Drawing Sheets

(52) U.S. Cl.
CPC .............. *A61F 2/2433* (2013.01); *A61F 2/95* (2013.01); *A61F 2/9522* (2020.05); *A61M 25/0147* (2013.01)

(58) Field of Classification Search
CPC . A61F 2/2439; A61F 2/2466; A61M 25/0147; A61M 2025/015; A61M 2025/0138
See application file for complete search history.

(56) References Cited

U.S. PATENT DOCUMENTS

| | | | |
|---|---|---|---|
| 4,955,384 A | 9/1990 | Taylor et al. | |
| 4,985,022 A | 1/1991 | Fearnot et al. | |
| 4,998,923 A | 3/1991 | Samson et al. | |
| 5,003,989 A | 4/1991 | Taylor et al. | |
| 5,035,706 A | 7/1991 | Giantureo et al. | |
| 5,095,915 A | 3/1992 | Engelson | |
| 5,315,996 A | 5/1994 | Lundquist | |
| 5,406,960 A | 4/1995 | Corso, Jr. | |
| 5,437,288 A | 8/1995 | Schwartz et al. | |
| 5,570,701 A | 11/1996 | Ellis et al. | |
| 5,599,492 A | 2/1997 | Engelson | |
| 5,665,115 A | 9/1997 | Cragg | |
| 5,702,419 A * | 12/1997 | Berry .................. | A61F 2/91 623/1.13 |
| 5,746,701 A | 5/1998 | Noone | |
| 5,749,837 A | 5/1998 | Palermo et al. | |
| 5,769,796 A | 6/1998 | Palermo et al. | |
| 5,772,609 A | 6/1998 | Nguyen et al. | |
| 5,776,080 A | 7/1998 | Thome et al. | |
| 5,800,456 A | 9/1998 | Maeda et al. | |
| 5,833,632 A | 11/1998 | Jacobsen et al. | |
| 5,902,254 A | 5/1999 | Magram | |
| 5,931,830 A | 8/1999 | Jacobsen et al. | |
| 5,951,494 A | 9/1999 | Wang et al. | |
| 6,001,068 A | 12/1999 | Uchino et al. | |
| 6,017,319 A | 1/2000 | Jacobsen et al. | |
| 6,139,510 A | 10/2000 | Palermo | |
| 6,221,096 B1 | 4/2001 | Aiba et al. | |
| 6,254,628 B1 | 7/2001 | Wallace et al. | |
| 6,273,876 B1 | 8/2001 | Klima et al. | |
| 6,398,776 B1 | 6/2002 | Sekino et al. | |
| 6,565,597 B1 | 5/2003 | Fearnot et al. | |
| 6,606,921 B2 | 8/2003 | Noetzold | |
| 6,739,787 B1 | 5/2004 | Bystrom | |
| 6,764,503 B1 | 7/2004 | Ishimaru | |
| 6,918,882 B2 | 7/2005 | Skujins et al. | |
| 6,921,397 B2 | 7/2005 | Corcoran et al. | |
| 7,055,656 B2 | 6/2006 | Drew | |
| 7,074,197 B2 | 7/2006 | Reynolds et al. | |
| 7,338,495 B2 | 3/2008 | Adams | |
| 7,413,563 B2 | 8/2008 | Corcoran et al. | |
| 7,533,906 B2 | 5/2009 | Luettgen et al. | |
| 7,540,865 B2 | 6/2009 | Griffin et al. | |
| 7,579,550 B2 | 8/2009 | Dayton et al. | |
| 7,618,379 B2 | 11/2009 | Reynolds et al. | |
| 7,625,364 B2 | 12/2009 | Corcoran et al. | |
| 7,780,611 B2 | 8/2010 | Griego et al. | |
| 7,784,376 B2 | 8/2010 | Wen | |
| 7,824,345 B2 | 11/2010 | Euteneuer et al. | |
| 7,841,994 B2 | 11/2010 | Skujins et al. | |
| 7,850,623 B2 | 12/2010 | Griffin et al. | |
| 7,854,109 B2 | 12/2010 | Zubiate et al. | |
| 7,914,466 B2 | 3/2011 | Davis et al. | |
| 7,914,467 B2 | 3/2011 | Layman et al. | |
| 7,918,080 B2 | 4/2011 | Zubiate et al. | |
| 7,993,286 B2 | 8/2011 | Reynolds et al. | |
| 8,022,331 B2 | 9/2011 | Reynolds et al. | |
| 8,047,236 B2 | 11/2011 | Perry | |
| 8,048,004 B2 | 11/2011 | Davis et al. | |
| 8,048,060 B2 | 11/2011 | Griffin et al. | |
| 8,080,053 B2 | 12/2011 | Satasiya et al. | |
| 8,099,939 B2 | 1/2012 | Zubiate et al. | |
| 8,100,031 B2 | 1/2012 | Zubiate et al. | |
| 8,105,246 B2 | 1/2012 | Voeller et al. | |
| 8,124,876 B2 | 2/2012 | Dayton et al. | |
| 8,137,293 B2 | 3/2012 | Zhou et al. | |
| 8,147,534 B2 | 4/2012 | Berez et al. | |
| 8,157,751 B2 | 4/2012 | Adams et al. | |
| 8,182,465 B2 | 5/2012 | Griffin et al. | |
| 8,192,422 B2 | 6/2012 | Zubiate et al. | |
| 8,197,419 B2 | 6/2012 | Field et al. | |
| 8,231,551 B2 | 7/2012 | Griffin et al. | |
| 8,257,279 B2 | 9/2012 | Davis et al. | |
| 8,292,829 B2 | 10/2012 | Griego et al. | |
| 8,317,777 B2 | 11/2012 | Zubiate et al. | |
| 8,328,868 B2 | 12/2012 | Paul et al. | |
| 8,376,865 B2 | 2/2013 | Forster et al. | |
| 8,376,961 B2 | 2/2013 | Layman et al. | |
| 8,377,035 B2 | 2/2013 | Zhou et al. | |
| 8,397,481 B2 | 3/2013 | Zubiate et al. | |
| 8,409,114 B2 | 4/2013 | Parins | |
| 8,414,506 B2 | 4/2013 | Reynolds et al. | |
| 8,425,408 B2 | 4/2013 | Boulais et al. | |
| 8,443,692 B2 | 5/2013 | Zubiate et al. | |
| 8,449,526 B2 | 5/2013 | Snyder et al. | |
| 8,459,138 B2 | 6/2013 | Zubiate et al. | |
| 8,475,366 B2 | 7/2013 | Boulais et al. | |
| 8,485,992 B2 | 7/2013 | Griffin et al. | |
| 8,535,219 B2 | 9/2013 | Smith et al. | |
| 8,535,243 B2 | 9/2013 | Shireman | |
| 8,551,020 B2 | 10/2013 | Chen et al. | |
| 8,551,021 B2 | 10/2013 | Voeller et al. | |
| 8,556,914 B2 | 10/2013 | Vrba | |
| 8,608,648 B2 | 12/2013 | Banik et al. | |
| 8,622,894 B2 | 1/2014 | Banik et al. | |
| 8,636,716 B2 | 1/2014 | Griffin et al. | |
| 8,656,697 B2 | 2/2014 | Zubiate et al. | |
| 8,677,602 B2 | 3/2014 | Dayton et al. | |
| 8,758,268 B2 | 6/2014 | Bown et al. | |
| 8,784,337 B2 | 7/2014 | Voeller et al. | |
| 8,795,202 B2 | 8/2014 | Northrop et al. | |
| 8,795,254 B2 | 8/2014 | Layman et al. | |
| 8,821,477 B2 | 9/2014 | Northrop et al. | |
| 8,833,197 B2 | 9/2014 | Zubiate et al. | |
| 8,845,552 B2 | 9/2014 | Griego et al. | |
| 8,864,654 B2 | 10/2014 | Kleiner et al. | |
| 8,870,790 B2 | 10/2014 | Davis et al. | |
| 8,900,163 B2 | 12/2014 | Jacobsen et al. | |
| 8,915,865 B2 | 12/2014 | Jacobsen et al. | |
| 8,932,235 B2 | 1/2015 | Jacobsen et al. | |
| 8,936,558 B2 | 1/2015 | Jacobsen et al. | |
| 8,939,916 B2 | 1/2015 | Jacobsen et al. | |
| 8,945,096 B2 | 2/2015 | Zubiate et al. | |
| 9,005,114 B2 | 4/2015 | Zubiate et al. | |
| 9,011,318 B2 | 4/2015 | Choset et al. | |
| 9,023,011 B2 | 5/2015 | Griffin et al. | |
| 9,072,874 B2 | 7/2015 | Northrop et al. | |
| 9,370,432 B2 | 6/2016 | Bennett et al. | |
| 9,375,234 B2 | 6/2016 | Vrba | |
| 9,386,911 B2 | 7/2016 | Zubiate et al. | |
| 9,387,308 B2 | 7/2016 | Hinchliffe et al. | |
| 9,387,309 B2 | 7/2016 | Parodi et al. | |
| 9,402,682 B2 | 8/2016 | Worrell et al. | |
| 9,993,360 B2 | 6/2018 | Shalev et al. | |
| 10,092,426 B2 | 10/2018 | McHugo | |
| 10,258,465 B2 | 4/2019 | Salahieh et al. | |
| 10,646,365 B2 | 5/2020 | Berra et al. | |
| 11,266,518 B2 | 3/2022 | Poppe et al. | |
| 12,016,777 B2 * | 6/2024 | Foster .................. | A61F 2/2466 |
| 2001/0037141 A1 | 11/2001 | Yee et al. | |
| 2003/0069520 A1 | 4/2003 | Skujins et al. | |
| 2003/0069521 A1 | 4/2003 | Reynolds et al. | |
| 2004/0064179 A1 | 4/2004 | Linder et al. | |
| 2004/0193244 A1 | 9/2004 | Hartley et al. | |
| 2004/0220499 A1 | 11/2004 | Griego et al. | |
| 2004/0243143 A1 | 12/2004 | Corcoran et al. | |
| 2005/0080400 A1 | 4/2005 | Corcoran et al. | |
| 2005/0090848 A1 | 4/2005 | Adams | |
| 2005/0267444 A1 | 12/2005 | Griffin et al. | |
| 2006/0111615 A1 | 5/2006 | Danitz et al. | |
| 2006/0122537 A1 | 6/2006 | Reynolds et al. | |
| 2006/0179966 A1 | 8/2006 | Kuo | |
| 2006/0189896 A1 | 8/2006 | Davis et al. | |

(56) References Cited

U.S. PATENT DOCUMENTS

| | | |
|---|---|---|
| 2007/0049902 A1 | 3/2007 | Griffin et al. |
| 2007/0066900 A1 | 3/2007 | O'Keeffe |
| 2007/0083132 A1 | 4/2007 | Sharrow |
| 2007/0100285 A1 | 5/2007 | Griffin et al. |
| 2007/0114211 A1 | 5/2007 | Reynolds et al. |
| 2007/0135734 A1 | 6/2007 | Reynolds et al. |
| 2007/0233043 A1 | 10/2007 | Dayton et al. |
| 2007/0244414 A1 | 10/2007 | Reynolds et al. |
| 2007/0265637 A1 | 11/2007 | Andreas et al. |
| 2008/0009829 A1 | 1/2008 | Ta et al. |
| 2008/0064989 A1 | 3/2008 | Chen et al. |
| 2008/0077119 A1 | 3/2008 | Snyder et al. |
| 2008/0194994 A1 | 8/2008 | Bown et al. |
| 2008/0205980 A1 | 8/2008 | Zubiate et al. |
| 2008/0245173 A1 | 10/2008 | Schwerin et al. |
| 2008/0255655 A1 | 10/2008 | Kusleika et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0143768 A1 | 6/2009 | Parodi et al. |
| 2009/0156999 A1 | 6/2009 | Adams et al. |
| 2009/0171151 A1 | 7/2009 | Choset et al. |
| 2009/0312606 A1 | 12/2009 | Dayton et al. |
| 2009/0319037 A1 | 12/2009 | Rowe et al. |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0234933 A1 | 9/2010 | Punga et al. |
| 2010/0249655 A1 | 9/2010 | Lemon |
| 2010/0274187 A1 | 10/2010 | Argentine |
| 2010/0286566 A1 | 11/2010 | Griffin et al. |
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0178588 A1 | 7/2011 | Haselby |
| 2011/0184241 A1 | 7/2011 | Zubiate et al. |
| 2011/0218620 A1 | 9/2011 | Meiri et al. |
| 2011/0257478 A1 | 10/2011 | Kleiner et al. |
| 2011/0264191 A1 | 10/2011 | Rothstein |
| 2012/0041411 A1 | 2/2012 | Horton et al. |
| 2012/0160537 A1 | 6/2012 | Wen |
| 2012/0265134 A1 | 10/2012 | Echarri et al. |
| 2013/0085562 A1 | 4/2013 | Rincon et al. |
| 2013/0123796 A1 | 5/2013 | Sutton et al. |
| 2013/0123912 A1 | 5/2013 | Tung et al. |
| 2013/0131775 A1 | 5/2013 | Hadley et al. |
| 2013/0144276 A1 | 6/2013 | Crisostomo et al. |
| 2014/0235361 A1 | 8/2014 | Forster et al. |
| 2015/0250481 A1 | 9/2015 | Chobotov |
| 2016/0100941 A1 | 4/2016 | Czyscon et al. |
| 2016/0184117 A1 | 6/2016 | Vad et al. |
| 2016/0256304 A1 | 9/2016 | Roeder et al. |
| 2016/0302921 A1 | 10/2016 | Gosal et al. |
| 2016/0317301 A1 | 11/2016 | Quadri et al. |
| 2018/0140323 A1 | 5/2018 | Foster et al. |

FOREIGN PATENT DOCUMENTS

| | | |
|---|---|---|
| EP | 2455128 A2 | 5/2013 |
| JP | 2001522694 A | 11/2000 |
| JP | 2001504016 A | 3/2001 |
| JP | 2010088545 A | 4/2010 |
| JP | 2011087947 A | 5/2011 |
| JP | 2012501725 A | 1/2012 |
| JP | 2012223578 A | 11/2012 |
| JP | 2013517910 A | 5/2013 |
| JP | 2013524943 A | 6/2013 |
| JP | 2014508568 A | 4/2014 |
| JP | 2014513585 A | 6/2014 |
| JP | 5575840 B2 | 8/2014 |
| JP | 2015500063 A | 1/2015 |
| JP | 2015501680 A | 1/2015 |
| JP | 2016067915 A | 5/2016 |
| JP | 2017507744 A | 3/2017 |
| WO | 9820811 A1 | 5/1998 |
| WO | 9925280 A1 | 5/1999 |
| WO | 2006041612 A2 | 4/2006 |
| WO | 2006073581 A2 | 7/2006 |
| WO | 2010027485 A1 | 3/2010 |
| WO | 2011094527 A1 | 8/2011 |
| WO | 2011133486 A1 | 10/2011 |
| WO | 20120966687 A1 | 7/2012 |
| WO | 2012116368 A2 | 8/2012 |
| WO | 2016196933 A1 | 12/2016 |
| WO | 2018170092 A1 | 9/2018 |
| WO | 2018204558 A1 | 11/2018 |

OTHER PUBLICATIONS

International Search Report and Written Opinion dated May 25, 2018 for International Application No. PCT/US2018/022371.
International Search Report and Written Opinion dated Jun. 15, 2018 for International Application No. PCT/US2018/022371.
International Search Report and Written Opinion dated Aug. 31, 2018 for International Application No. PCT/US2018/030751.
International Search Report and Written Opinion dated Jun. 27, 2019 for International Application No. PCT/US2019/029336.
International Search Report and Written Opinion dated Aug. 16, 2018 for international Application No. PCT/US2019/029345.
Notice of Reasons for Refusal dated Dec. 14, 2021 for Japanese Patent Application No. 2020-0559546.

\* cited by examiner

MEDICAL DEVICE INCLUDING ATTACHABLE COMPONENTS

CROSS-REFERENCE TO RELATED APPLICATIONS

This application claims the benefit of priority of U.S. Provisional Application No. 63/141,795 filed Jan. 26, 2021, the entire disclosure of which is hereby incorporated by reference.

TECHNICAL FIELD

The present disclosure pertains to medical devices, and methods for manufacturing medical devices. More particularly, the present disclosure pertains to medical devices including an attachable inner member and attachable outer member.

BACKGROUND

A wide variety of intracorporeal medical devices have been developed for medical use, for example, intravascular use. Some of these devices include heart valves, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example system for delivering an implantable heart valve includes a connection assembly having an engaged configuration and a disengaged configuration, the connection assembly including: an inner shaft having a proximal end region, a distal end region and a first coupling member disposed along a portion of the distal end region, wherein the first coupling member includes a plurality of apertures. The connection assembly also includes a support shaft having a proximal end region, a distal end region and a second coupling member disposed along a portion of the proximal end region, wherein the second coupling member includes a stem, wherein the stem includes a groove extending circumferentially around the stem. The connection assembly also includes a plurality of bearings, wherein each bearing is disposed in a respective aperture of the plurality of apertures, and wherein a portion of each bearing is also disposed in a portion of the groove when the connection assembly is in the engaged configuration. The connection assembly also includes a locking cap coupled to the inner shaft, wherein a portion of the locking cap is configured to cover at least a portion of each of the plurality of bearings when the connection assembly is in the engaged configuration.

Alternatively or additionally to any of the embodiments above, wherein the locking cap includes a plurality of tabs extending circumferentially around a longitudinal axis of the locking cap.

Alternatively or additionally to any of the embodiments above, wherein the each of the plurality of tabs is configured to flex radially away from the longitudinal axis.

Alternatively or additionally to any of the embodiments above, wherein each of the plurality of tabs is configured to flex radially away from the longitudinal axis as the stem in inserted into a lumen of the first coupling member.

Alternatively or additionally to any of the embodiments above, wherein each of the plurality of tabs is configured to exert a radially inward force on each of the plurality of bearings in the engaged configuration.

Alternatively or additionally to any of the embodiments above, wherein each of the plurality of bearings is configured to slide circumferentially around the stem while disposed within the groove.

Alternatively or additionally to any of the embodiments above, wherein each of the bearings is configured to rotate relative to the first coupling member, the second coupling member and the locking cap in the engaged configuration.

Alternatively or additionally to any of the embodiments above, wherein each of the bearings is configured to shift radially outward within its respective aperture of the plurality of apertures as the stem is inserted into a lumen of the first coupling member.

Alternatively or additionally to any of the embodiments above, wherein each of the plurality of bearings is disposed within its respective aperture of the plurality of apertures in the disengaged configuration.

Alternatively or additionally to any of the embodiments above, wherein the locking cap is fixedly attached to the first actuation coupling member.

Alternatively or additionally to any of the embodiments above, wherein the first coupling member is configured to rotate relative to the second coupling member in the engaged configuration.

Another system for delivering an implantable heart valve includes a tip assembly having a distal end region and a proximal end region, a guidewire shaft coupled to the distal end region of the tip assembly and a connection assembly having an engaged configuration and a disengaged configuration, the connection assembly including: an inner shaft having a proximal end region, a distal end region and a first coupling member disposed along a portion of the distal end region, wherein the first coupling member includes a plurality of apertures. The connection assembly also includes a support shaft having a proximal end region, a distal end region and a second coupling member disposed along a portion of the proximal end region, wherein the second coupling member includes a stem, wherein the stem includes a groove extending circumferentially around the stem. The connection assembly also includes a plurality of bearings, wherein each bearing is disposed in a respective aperture of the plurality of apertures, and wherein a portion of each bearing is also disposed in a portion of the groove when the connection assembly is in the engaged configuration. The connection assembly also includes a locking cap coupled to the inner shaft, wherein a portion of the locking cap is configured to cover at least a portion of each of the plurality of bearings when the connection assembly is in the engaged configuration.

Alternatively or additionally to any of the embodiments above, wherein the locking cap includes a plurality of tabs extending circumferentially around a longitudinal axis of the locking cap.

Alternatively or additionally to any of the embodiments above, wherein each of the plurality of tabs is configured to flex radially away from the longitudinal axis.

Alternatively or additionally to any of the embodiments above, wherein each of the plurality of tabs is configured to flex radially away from the longitudinal axis as the stem in inserted into a lumen of the first coupling member.

Alternatively or additionally to any of the embodiments above, wherein each of the plurality of tabs is configured to exert a radially inward force on each of the plurality of bearings in the engaged configuration.

Alternatively or additionally to any of the embodiments above, wherein each of the plurality of bearings is configured to slide circumferentially around the stem while disposed within the groove.

Alternatively or additionally to any of the embodiments above, wherein each of the bearings is configured to rotate relative to the first coupling member, the second coupling member and the locking cap in the engaged configuration.

Alternatively or additionally to any of the embodiments above, wherein the first coupling member is configured to rotate relative to the second coupling member in the engaged configuration.

An example method for delivering an implantable heart valve includes attaching a first coupling member of an actuation shaft to a second coupling member of a support shaft of a medical device delivery system, the medical device delivery system including the implantable heart valve, wherein attaching the first coupling member of the actuation shaft to the second coupling member of the support shaft includes positioning a plurality of bearings into a groove of the second coupling member. The method also includes advancing the medical device delivery system to a target site adjacent the heart; and deploying the implantable heart valve at the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
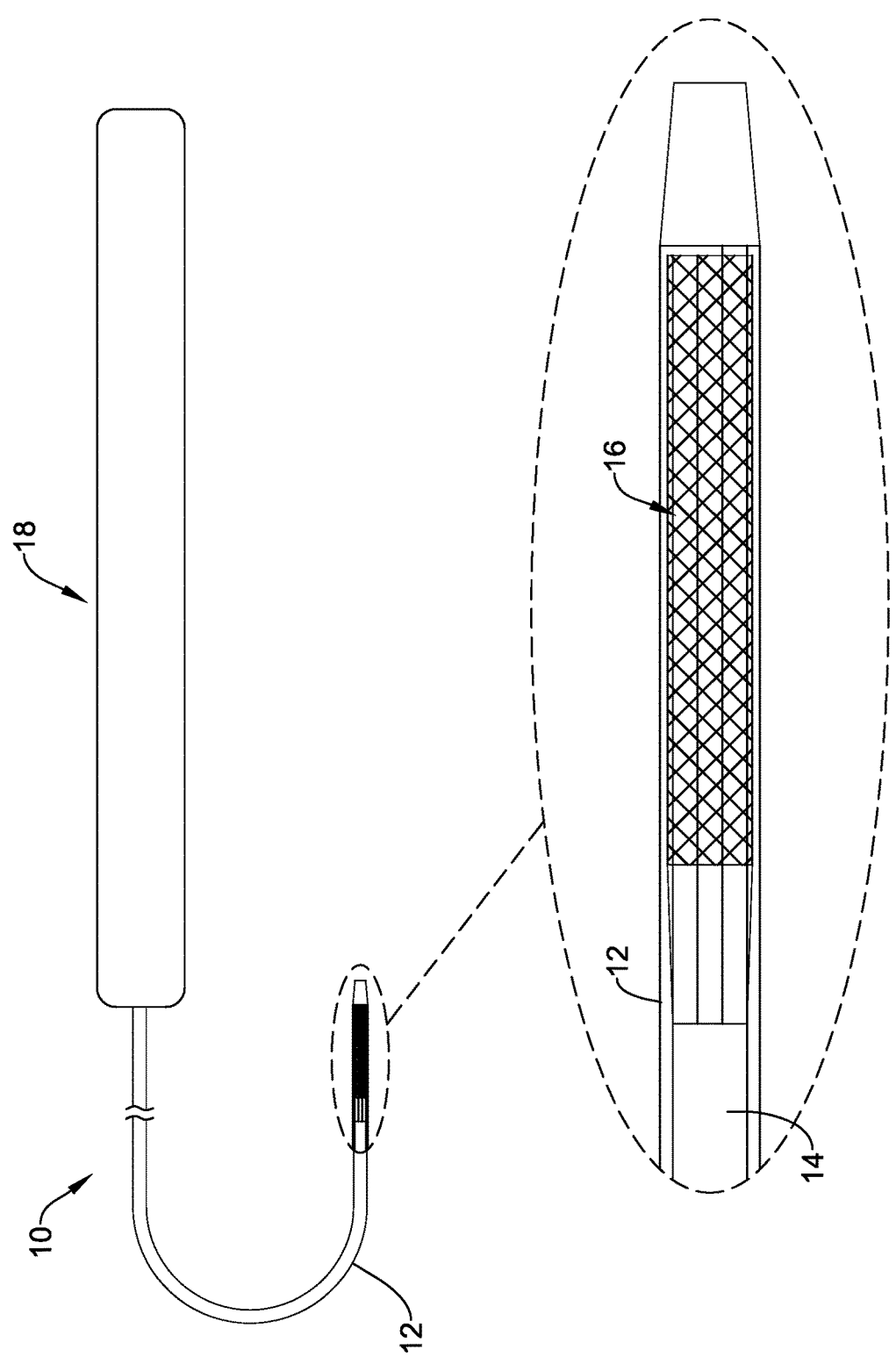
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the body. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed. For example, therapies have been developed which allow a blocked coronary artery to be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1, for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16 (shown in the detailed view of FIG. 1), such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer shaft 12, an exoskeleton 14 extending at least partially through a lumen of the outer shaft 12, and a medical implant 16 (e.g., a replacement heart valve implant) which may be coupled to the exoskeleton 14 and disposed within a lumen of the outer shaft 12 during delivery of the medical implant 16. In some embodiments, a medical device handle 18 may be disposed at a proximal end of the outer shaft 12 and/or the exoskeleton 14 and may include one or more actuation mechanisms associated therewith. In other words, one or more tubular members (e.g., the outer shaft 12, the exoskeleton 14, etc.) may extend distally from the medical device handle 18. In general, the medical device handle 18 may be designed to manipulate the position of the outer shaft 12 relative to the exoskeleton 14 and/or facilitate the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer shaft 12, as seen schematically in FIG. 1, for example. Once positioned, the outer shaft 12 may be retracted relative to the medical implant 16 and/or the exoskeleton 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 18 in order to translate the medical implant 16 into a generally shortened and larger profile "deployed" configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system (e.g., the medical device system 10) may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

In some instances, it may be desirable to design the medical device system 10 such that one or more device components may be disconnected from the medical device handle 18 when initially packaged (e.g., unattached to the exoskeleton 14, other inner shafts, etc.) whereby the one or more components may be subsequently coupled to the handle 18 after the packaging containing the medical device system 10 has been opened (and prior to a clinician utilizing the medical device system 10 in a medical procedure). For example, in some instances it may be desirable to package the medical implant 16 (e.g., heart valve, heart valve frame, the heart valve support structure, etc.) separately prior to performing the medical procedure. It can be appreciated that packaging the medical implant 16 (e.g., heart valve, heart valve frame, the heart valve support structure, etc.) separately may permit the medical implant 16 (including the heart valve, heart valve frame, the heart valve support structure, etc.) to be sterilized according to a different process, or kept at different temperatures, for example, than the remaining separately-packaged components of the medical device system 10.

Figure 2:
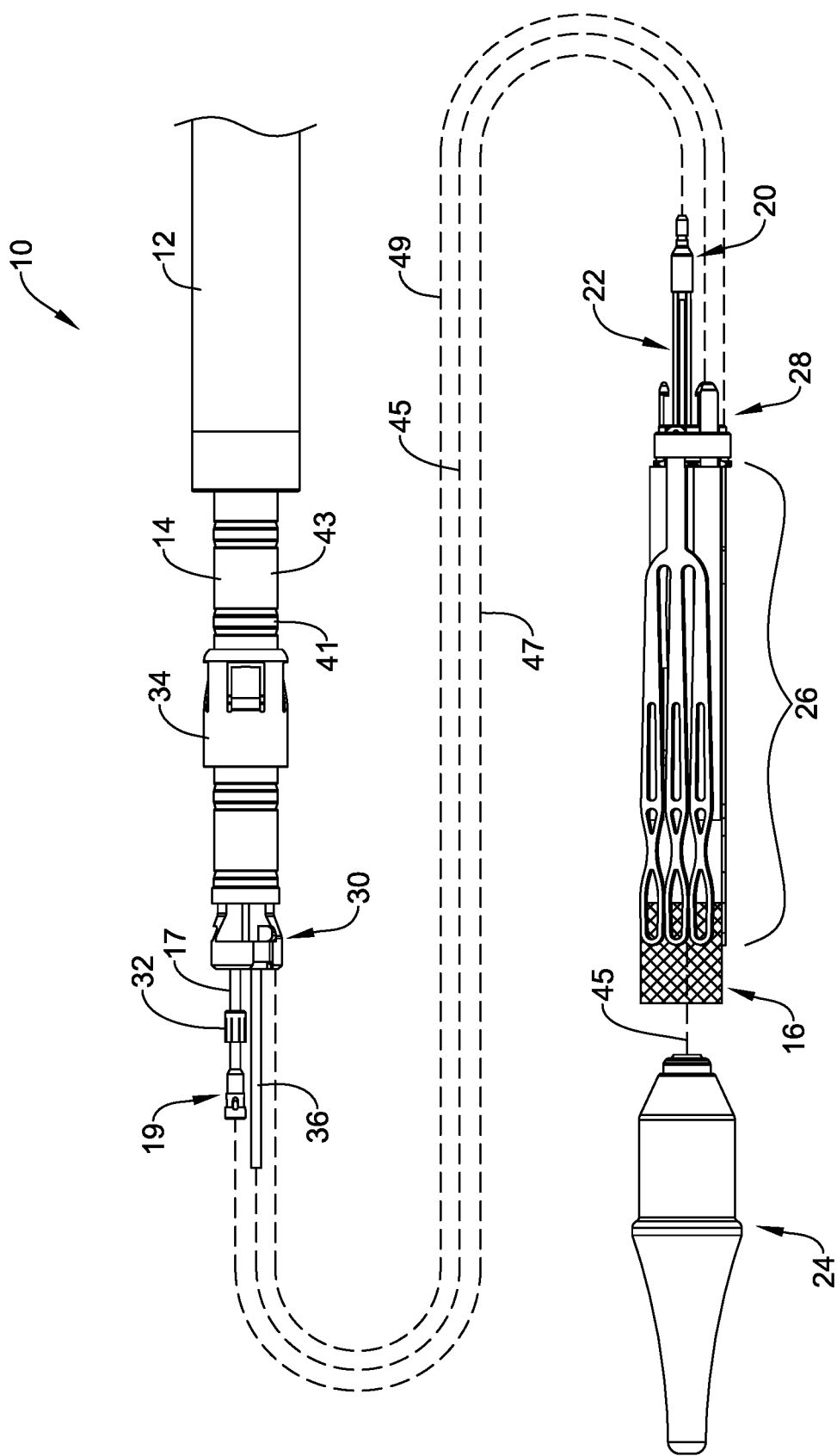
FIG. 2 is a side view of the tip assembly and valve assembly spaced away from the inner shaft and exoskeleton of the medical device of FIG. 1.

FIG. 2 shows an illustration of the medical device system 10 whereby the medical implant 16, the medical implant support structure 26 (coupled to the medical implant 16) and the tip assembly 24 are uncoupled from the handle 18 (it is noted that, for simplicity, the handle 18 is not shown in FIG. 2). It can be appreciated from FIG. 2 that any one of the medical implant 16, the medical implant support structure 26 and/or the tip assembly 24 may be packaged separately from the remaining components (e.g., handle 18, outer shaft 12, exoskeleton 14, guidewire shaft 36, etc.) of the medical device system 10, as described above.

As discussed above, FIG. 2 illustrates that the tip assembly 24 is uncoupled (e.g., unattached) from the medical implant 16, the medical implant support structure 26 and the remainder of the medical device delivery system 10. For example, in the packaging of the medical device system 10, the tip assembly may be packaged separately from the remainder of the medical device system 10. However, FIG. 2 further illustrates that the tip assembly 24 may eventually be coupled to the handle member 18 (and remainder of the medical device system 10) via a tubular guidewire member 36 (as illustrated by the dotted line 45).

In some examples, the tubular guidewire member 36 may extend proximally within the lumen of an exoskeleton 14 and couple to the handle member 18 (it is noted that the exoskeleton 14 will be discussed in greater detail below). Additionally, the tubular guidewire member 36 may include a lumen which permits a guidewire to extend and translate therein. In other words, when fully assembled, the medical device system 10 may be advanced to a target site within a body over a guidewire extending within the lumen of the tubular guidewire member 36. Further, as discussed above, the tubular guidewire member 36 may extend from the handle member 18, through the lumen of the exoskeleton 14, through the implant medical and terminate at the tip assembly 24. Additionally, to attach the tubular guidewire member 36 to the tip assembly 24, the tubular guidewire member 36 may be advanced through the medical implant support structure 26 and the medical implant 16. Further, the tip assembly 24 and the tubular guidewire member 36 may be designed such that they "quick connect" (e.g., snap, attach, engage, etc.) together. Examples of attaching the tip assembly to a tubular guidewire member 36 are disclosed in U.S. Patent Application No. 62/887,088, the entirety of which is incorporated by reference.

As discussed above, FIG. 2 further illustrates the medical implant 16 (e.g., a heart valve) coupled to a medical implant support structure 26. FIG. 2 illustrates that the medical implant 16 and the medical implant support structure 26 are uncoupled (e.g., unattached) from the remainder of the medical device delivery system 10. In the configuration shown, it can be appreciated that the medical implant support structure 26 may include one or more components and/or features which are designed to maintain the medical implant 16 in a pre-delivery configuration prior to attaching the medical implant 16 and medical implant support structure 26 to the remainder of the medical device system 10.

While FIG. 2 illustrates the medical implant 16 and the medical implant support structure 26 unattached to the remainder of the medical device system 10, it can be appreciated that the medical implant 16 and the medical implant support structure 26 may be coupled to the remainder of the medical device system 10 (e.g., handle 18) via one or more shaft members and/or coupling members (as illustrated by the dotted line 49). The coupling of the medical implant 16 and the medical implant support structure 26 to the medical device system 10 will be described below.

For example, as discussed above, FIG. 2 illustrates that the medical device system 10 may include an exoskeleton 14 extending within the outer shaft 12. The exoskeleton 14 may include one more lumens extending therein. One or more inner shafts may extend through the exoskeleton 14. For example, the exoskeleton 14 may include a lumen through which an actuation shaft 17 may extend (the actuation shaft 17 will be described in greater detail below).

Further, in some examples, the exoskeleton 14 may include a plurality of discrete members or articulating links. For example, the exoskeleton 14 may include a plurality of bead members 41 and a plurality of barrel members 43. Other discrete members are contemplated that may have differing shapes and/or configurations. In general, the discrete members (e.g., the bead members 41 and the barrel members 43) are engaged with one another and are designed to increase the compression resistance, the tension resistance, or both of the exoskeleton 14 while also affording a desirable amount of flexibility and kink resistance such that the one or more inner shafts extending through the exoskeleton can be navigated through the anatomy. The bead members 41 and the barrel members 43 may be arranged in a number of different configurations. In at least some instances, the bead members 41 and the barrel members 43 alternate along the exoskeleton 14. Other arrangements and/or patterns are contemplated. Example exoskeletons are disclosed in U.S. Patent Publication No. US20180140323, the entirety of which is incorporated by reference.

Additionally, FIG. 2 illustrates that, in some examples, the distal end of the exoskeleton 14 may include a first exoskeleton coupling member 30. As will be described in greater detail below, the first exoskeleton coupling member 30 may include one or more features which are designed to attach to a second exoskeleton coupling member 28. As further illustrated in FIG. 2, the second exoskeleton coupling member 28 may be attached to the proximal end of one or more components of the medical implant support structure 26. Therefore, it can be appreciated that coupling the first exoskeleton coupling member 30 to the second exoskeleton coupling member 28 may connect the exoskeleton 14 to the medical implant 16 via the medical implant support structure 26.

Additionally, as will be described in greater detail below, FIG. 2 illustrates that the medical device system 10 may include an exoskeleton locking collar 34. The exoskeleton locking collar 34 may be disposed along an outer surface of the exoskeleton 14. As will be described in greater detail below, the exoskeleton locking collar 34 may be utilized to couple (e.g., attach, lock, engage, etc.) the first exoskeleton coupling member 30 to the second exoskeleton coupling member 28.

It is noted that FIG. 2 illustrates the outer shaft 12 of the medical device system 10 having been retracted in a proximal direction to a position proximal of both the first exoskeleton coupling member 30, the exoskeleton locking collar 34, a portion of the actuation shaft 17 and a portion of the tubular guidewire member 36. It can be appreciated that when all the components of the medical device system 10 (including the medical implant 16, the medical implant support structure 26 and the tip assembly 24) are assembled, the outer shaft 12 may be advanced distally such that it covers the medical implant 16, the medical implant support structure 26 and a portion of the tip assembly 24.

Additionally, as discussed above, FIG. 2 illustrates that the medical device system 10 may include an actuation shaft 17 extending within a portion of the exoskeleton 14. FIG. 2 further illustrates that, in some examples, the distal end of the actuation shaft 17 may include a first actuation shaft coupling member 19. As will be described in greater detail below, the first actuation shaft coupling member 19 may include one or more features which are designed to attach to a second actuation shaft coupling member 20. As further illustrated in FIG. 2, the second actuation coupling member 20 may be attached to the proximal end of one or more translation members 22 (e.g., push-pull members). Therefore, it can be appreciated that coupling the first actuation shaft coupling member 18 to the second actuation coupling member 20 may connect the actuation shaft 17 to the medical implant 16 via the one or more translation members 22 (as illustrated by the dotted line 47).

In some examples, an operator may be able to manipulate the translation members 22 via the handle 18 (which is coupled to the translation members 22 via the actuation shaft 17, first actuation coupling member 19 and second actuation coupling member 20). For example, the handle 18 may be designed to control the translation of the translation members 22. Further, actuation of the translation members 22 may help deploy the medical implant 16 at a target site adjacent the heart. Example translation members are disclosed in U.S. patent application Ser. No. 16/396,089, the entirety of which is incorporated by reference.

Additionally, as will be described in greater detail below, FIG. 2 illustrates that the medical device system 10 may include an actuation shaft locking cap 32. The actuation shaft locking cap 32 may be disposed along an outer surface of the actuation shaft 17. As will be described in greater detail below, the actuation shaft locking cap 32 may be utilized to couple (e.g., attach, lock, engage, etc.) the first actuation shaft coupling member 19 to the second actuation coupling member 20.

In some instances, the order of connecting separately packaged components may include first advancing the guidewire shaft 36 through the medical implant. Next, the first actuation coupling member 19 may be attached to the second actuation coupling member 20. After this connection is made, the actuation shaft 17 may be retracted such that the first exoskeleton coupling member 30 may be attached to the implant support structure 26 via the second exoskeleton coupling member 28. Finally, the nosecone 24 may be attached to the distal end region of the guidewire shaft 36.

Figure 3:
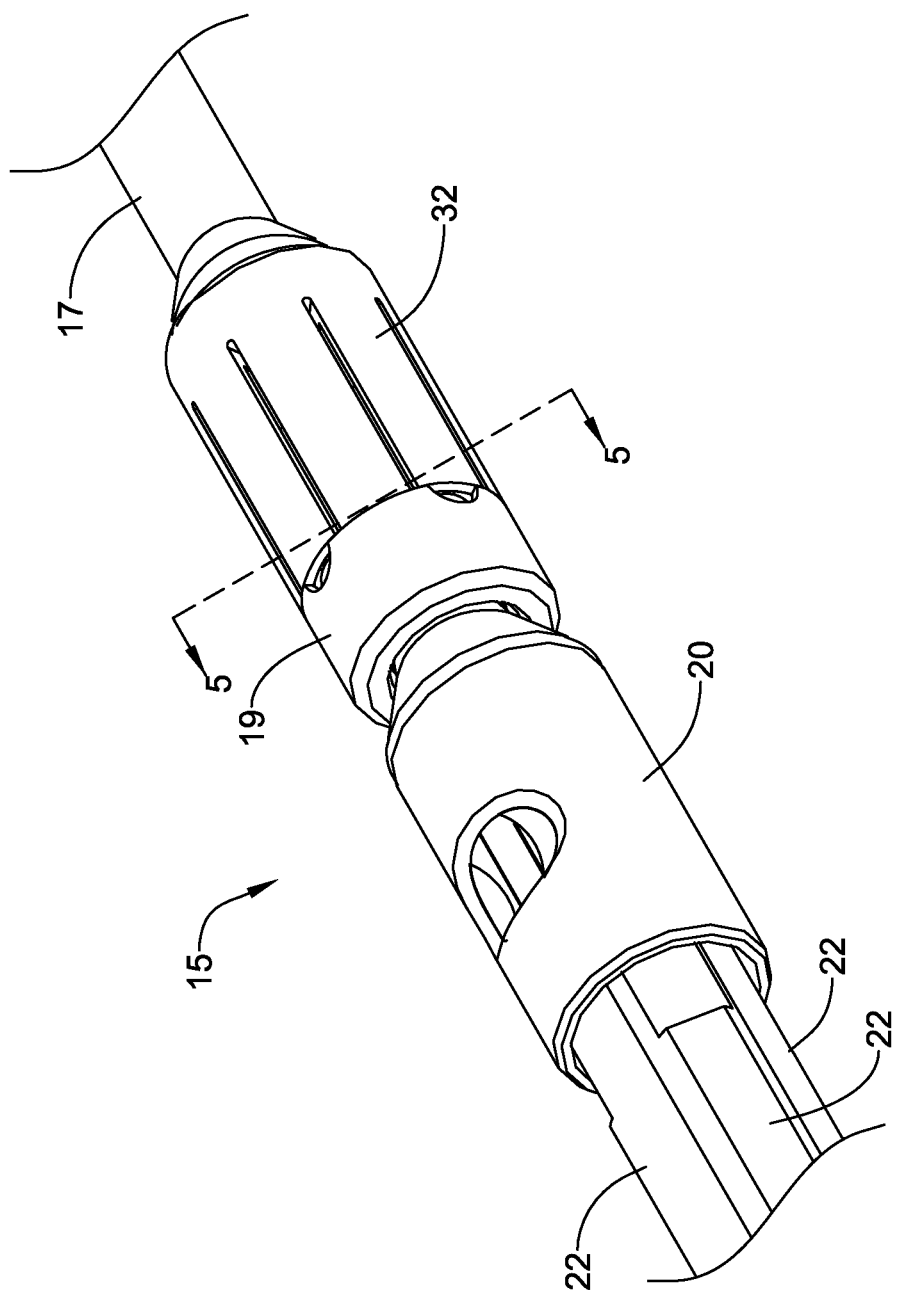
FIG. 3 is a perspective view of a connection assembly of the medical device of FIG. 1.

FIG. 3 is a perspective view showing a connection assembly 15. Specifically, FIG. 3 illustrates the first actuation coupling member 19 coupled to the second actuation coupling member 20. As shown in FIG. 3, the proximal end of the first actuation coupling member 19 may be attached to the distal end of the actuation shaft 17. It can be appreciated from FIG. 3 that the first actuation coupling member 19 may include a lumen (not visible in FIG. 3, but shown in FIG. 4) extending therein. It can be further appreciated from FIG. 3 that the distal end region of the second actuation coupling member 20 may include a stem (not visible in FIG. 3, but shown in FIG. 4) which is configured to be inserted into the lumen of the first actuation coupling member 19. A more detailed description of the first actuation coupling member 19 coupled to the second actuation coupling member 20 is provided below.

Additionally, FIG. 3 illustrates the actuation shaft locking cap 32 disposed along the outer surface of the first actuation coupling member 19. in some examples, the actuation shaft locking cap 32 may be fixedly attached (e.g., welded) to the first actuation coupling member 19. As will be described in greater detail below, the actuation shaft locking cap 32 may be designed such that both the actuation shaft 17 and the proximal end region of the first actuation coupling member 19 may extend through a portion of the actuation shaft locking cap 32 (e.g., a portion of the actuation shaft locking cap 32 may extend circumferentially around the outer surface of the first actuation coupling member 19). Additionally, FIG. 3 illustrates that the actuation shaft locking cap 32 may include one or more tabs 32 circumferentially spaced around the longitudinal axis of the locking cap 32. Further details of the actuation locking cap 32 and its engagement with both the first actuation coupling member 19 and the second actuation coupling member 20 are discussed below.

FIG. 3 further illustrates that the proximal end of the second actuation coupling member 20 may be attached to the distal ends of each of the translation members 22 described above. For example, it can be appreciated from FIG. 3 that the proximal end of the second actuation coupling member 20 may include a lumen (not visible in FIG. 3) within which the distal end region of each of the translation members 22 may be inserted. Additional details of the engagement of the second actuation coupling member 20 with the translation members 22 is described below.

Figure 4:
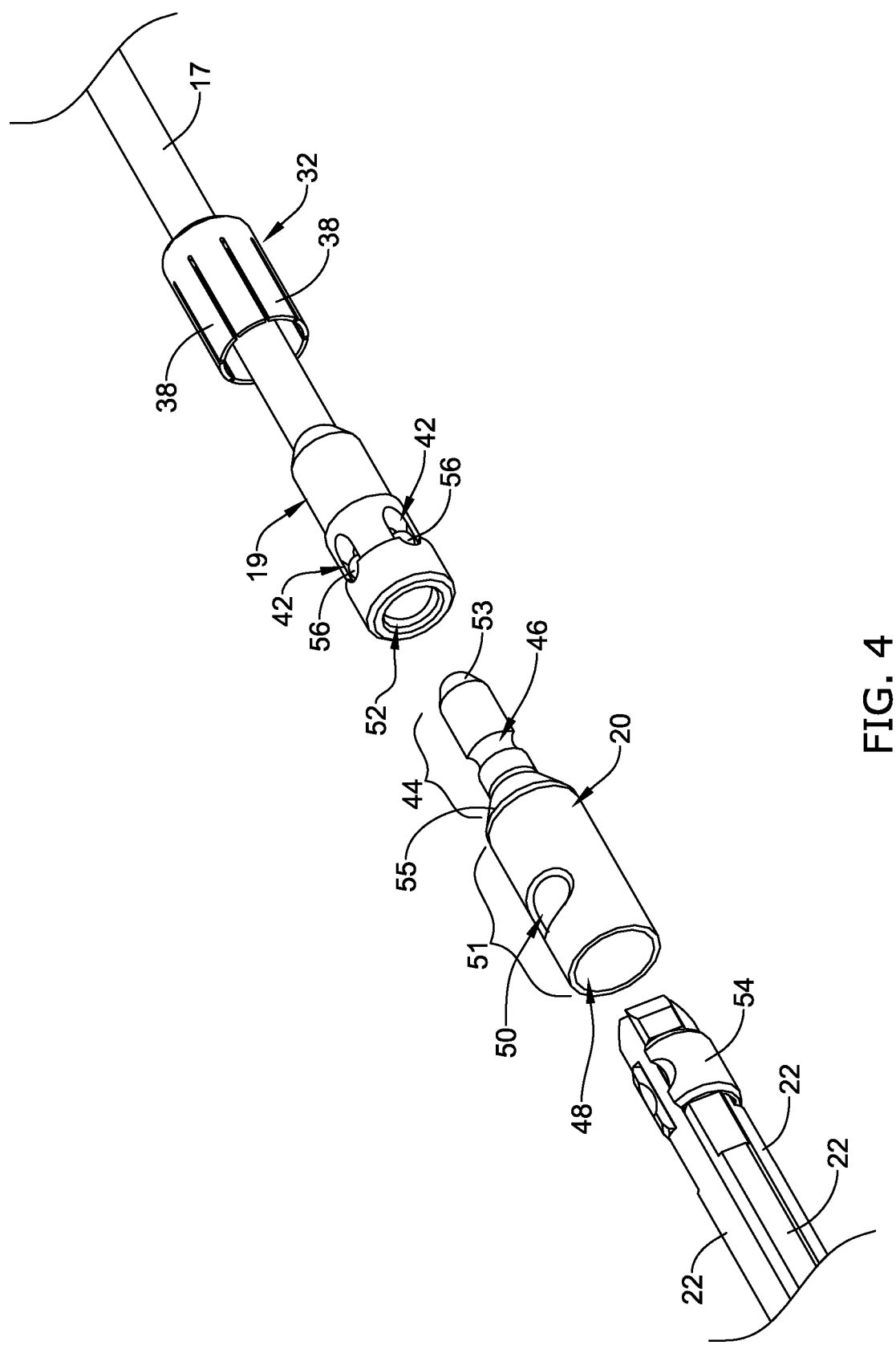
FIG. 4 is an exploded view of the connection assembly shown in FIG. 3.

FIG. 4 illustrates an exploded view of the connection assembly 15 shown in FIG. 3. Specifically, FIG. 4 illustrates the translation members 22 (coupled to one another via a securement collar 54) aligned with the second actuation coupling member 20, the second actuation coupling member 20 aligned with the first actuation coupling member 19, and the actuation shaft locking cap 32 positioned proximal of the first actuation coupling member 19 and disposed along the actuation shaft 17.

FIG. 4 illustrates the translation members 22 aligned with the lumen 48 of the second actuation coupling member 20. It is noted that FIG. 4 illustrates three translation members 22 positioned adjacent to one another (however, one of the translation members 22 is partially obstructed from view as it is positioned behind two other translation members 22 in the illustration). FIG. 4 further illustrates that the translation members 22 may be secured to one another via a securement collar 54. The securement collar 54 may extend around all or a portion of the outer surface of the translation members 22. Details of the engagement of the securement collar 54 and the translation members 22 is discussed with respect to FIG. 7 below.

FIG. 4 further illustrates the second actuation coupling member 20 having a proximal end region 51 and a distal end region 44. Additionally, the second actuation coupling member 20 may include a lumen 48 extending within a portion of the proximal end region 51. As discussed above, the lumen 48 of the second actuation coupling member 20 may be sized to permit the distal end regions (including the securement collar 54) of the translation members 22 to be inserted therein. It can be further appreciated from FIG. 4 that the distal ends of the translation members 22 may include a tapered (e.g., chamfered, beveled, angled, etc.) distal end which may permit easier insertion of the distal ends of the translation members 22 into the lumen 48 of the second actuation coupling member 20.

In some instances, the translation members 22 may be secured to the second actuation coupling member 20 via welding the securement collar 54 directly to the second actuation coupling member 20. Further, in some examples, the aperture 50 may be utilized during the welding process to assure that the securement collar 54 is properly aligned with the second actuation coupling member 20.

As discussed above, FIG. 4 illustrates that the distal end region 44 of the second actuation coupling member 20 may be referred to as a stem extending away from the proximal end region 51. As shown in FIG. 4, the stem 44 may include an outer diameter which is less than the diameter of the lumen 48 of the proximal end region 51. Additionally, in some examples, the second actuation coupling member 20 may include a tapered lip 55 which is positioned between the proximal end region 51 and the stem 44.

FIG. 4 further illustrates that the stem 44 may include a groove 46 which extends circumferentially around the circumference of the stem 44. The groove 46 may be described as a portion of the stem 44 which extends radially inward from an outer surface of the stem 44. Further, FIG. 4 illustrates that the groove 46 may be positioned along the stem 44 such that it is positioned approximately midway along the length of the stem 44.

However, this is not intended to be limiting. The groove 46 may be positioned along any portion of the stem 44. Additionally, FIG. 4 illustrates that the stem 44 may include a tapered (e.g., chamfered, beveled, angled, etc.) distal end 53 which may permit easier insertion of the distal end of the stem 44 into the lumen 52 of the first actuation coupling member 19.

FIG. 4 further illustrates the first actuation coupling member 19 aligned with the second actuation coupling member 20. As discussed above, the first actuation coupling member 19 may include a lumen 52 which may be configured to accept the stem 44 of the second actuation coupling member 20 therein. In other words, the lumen 52 may include a diameter which is sized to the permit the outer diameter of the stem 44 be inserted therein.

FIG. 4 further illustrates that the first actuation coupling member 19 may include one or more apertures 42 which extend from the outer surface of the first actuation coupling member 19, through the wall of the first actuation coupling member 19 to an inner surface of the first actuation coupling member 19. In other words, each aperture 42 extends from the outer surface of the first actuation coupling member 19 and opens into the lumen 52 of the first actuation coupling member 19. Each of the apertures 42 may be spaced away from one another around the circumference of the first actuation coupling member 19. For example, the first actuation coupling member 19 may include 1, 2, 3, 4, 5, 6, 7, 8, 9, 10 or more apertures 42, whereby the apertures 42 may be evenly spaced (e.g., symmetrically spaced) around the circumference of the first actuation coupling member 19. However, in other examples the apertures 42 may be unevenly spaced around the circumference of the first actuation coupling member 19. FIG. 4 further illustrates the actuation shaft locking cap 32 disposed along the actuation shaft 17.

FIG. 4 further illustrates that one or more spherical bearings 56 may be positioned within each aperture 42. The bearings 56 may designed to freely spin while positioned within the aperture 42. Additionally, as will be shown in FIG. 5 below, each bearing 56, while positioned within its respective aperture 42, may extend radially inward (through the aperture 42) such that a portion of each bearing 56 may nest within the groove 46, while also being prevented from "falling through" its respective aperture 42. This feature will be discussed in greater detail with respect to FIG. 5 below.

Further, it can be appreciated that each individual bearing 56 may be designed to rotate, slide, spin, translate both within the aperture 42 and while nested within the groove 46. Additionally, the bearings 56 may be designed to rotate around the circumference of the stem 44 while remaining within both the apertures 42 and the groove 46. In other words, each of the bearings 56 may be permitted to travel around the outer surface of the stem 44 within the groove 46, and while doing so, each individual bearing 56 may be spinning, sliding, rotating, etc. Referring back to FIG. 3, a portion of the locking cap 32 may extend overtop of each of the spherical bearings 56, and therefore, may prevent each bearing from "falling out" of the upper opening of the aperture 42. For example, the locking cap 32 may include one or more locking tabs 38 which may extend overtop of each of the spherical bearings 56.

Figure 5:
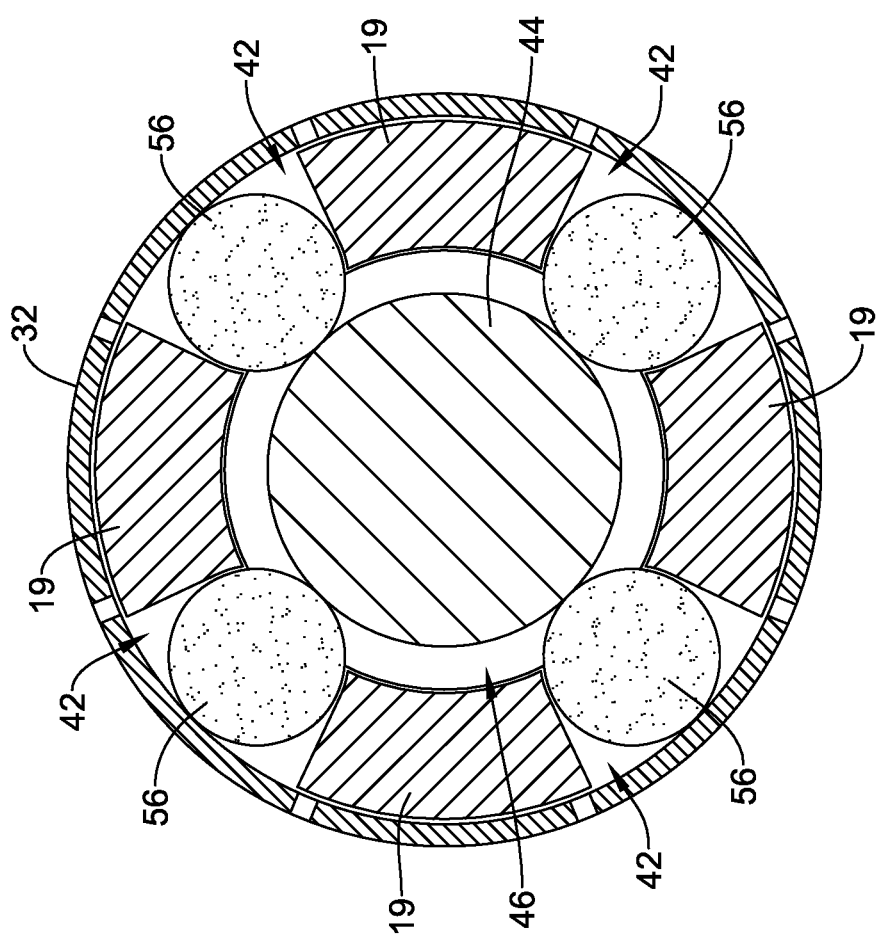
FIG. 5 is a cross-sectional view taken along line 5-5 of FIG. 3.

FIG. 5 illustrates a cross-sectional of the connection assembly 15 taken along line 5-5 of FIG. 3. FIG. 5 illustrates each of the spherical bearings 56 positioned within the aperture 42 of the first actuation coupling member 19. Additionally, as described above, FIG. 5 illustrates a portion of each spherical bearing extending radially inward of the inner surface of the first actuation coupling member 19 (the inner surface of coupling member 19 defining the lumen 52 shown in FIG. 4) such that each spherical bearing 56 rests within the groove 46 of the stem 44. It can be appreciated from FIG. 5 that the apertures 42 are designed to permit only a portion of each spherical bearing to extend into the groove 46 (e.g., the spherical bearings are prevented from falling through the apertures 42 and into the lumen 58 when the stem 44 is removed from the lumen 52).

FIG. 5 further illustrates the locking cap 32 being positioned overtop of both the first actuation coupling member 19 and each of the spherical bearings 56. It can eb appreciated that the locking cap 32 may be designed to prevent each of the spherical bearings 56 from falling out of the aperture in which it is positioned while also permitting the bearing to spinning, sliding, rotating, etc. within the aperture 42 and the groove 46.

Figure 6:
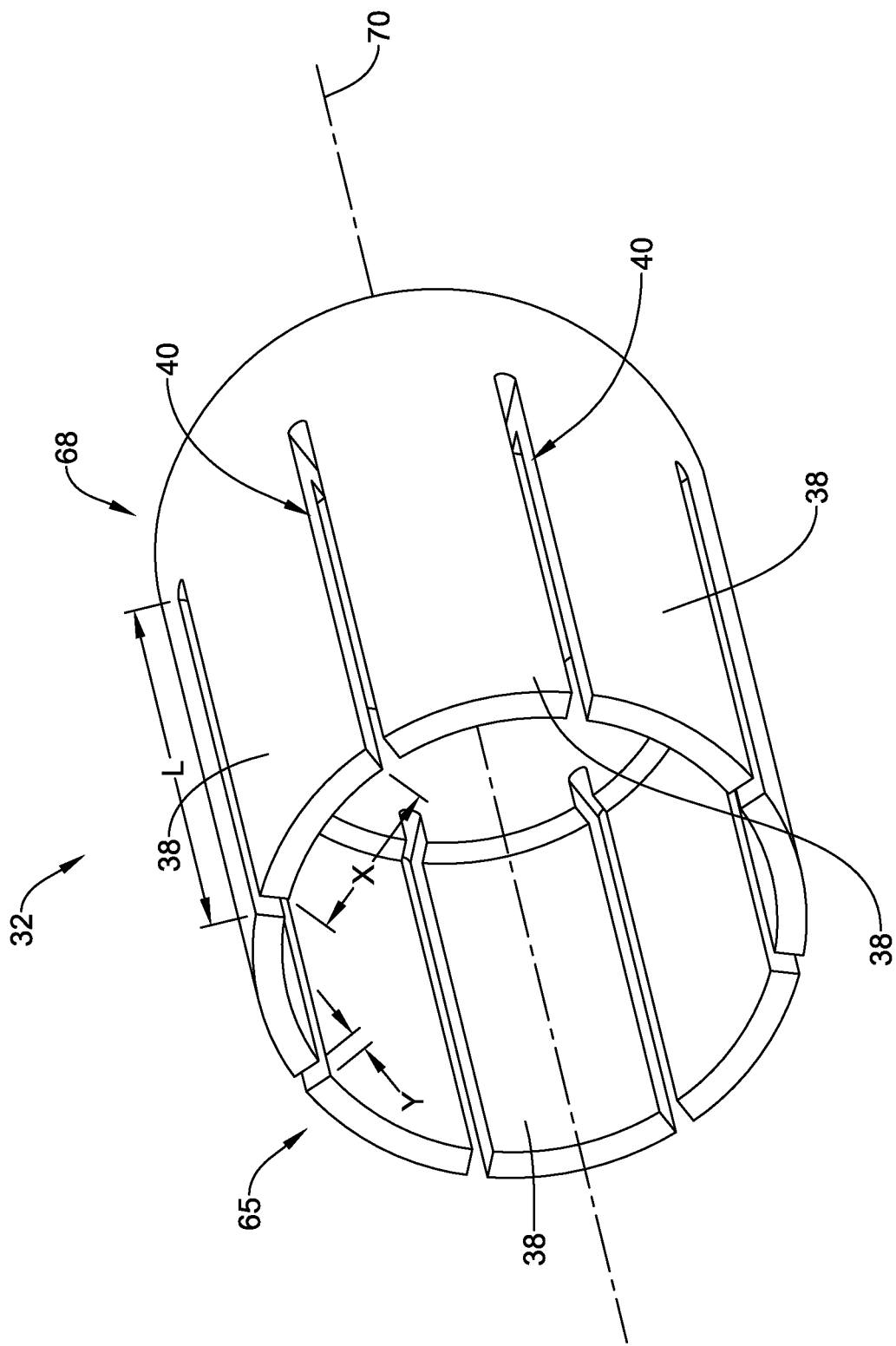
FIG. 6 is a perspective view of an example component of the connection assembly shown in FIGS. 3-4.

FIG. 6 illustrates a detailed view of the actuation shaft locking cap 32. As shown in FIG. 6, the actuation shaft locking cap 32 may include a first end 68, a second end 65 opposite the first end 68, and one or more locking tabs 38 extending along the longitudinal axis from the first end 68 to the second end 65. As shown in FIG. 6, the locking tabs 38 may be arranged circumferentially around the longitudinal axis 70 of the locking cap 32. In some examples, the locking cap 32 may include one or more gaps 40 extending along the longitudinal axis 70, whereby each gap 40 separates two individual locking tabs 38.

It can be appreciated that FIG. 6 illustrates that each locking tab 38 may have a uniform arc length X (around the longitudinal axis 70) and that each gap 40 may have a uniform arch width Y (around the longitudinal axis 70), this is not intended to be limiting. Rather, it is contemplated that the one or more locking tabs 38 may include variable arc lengths (e.g., the arc lengths X of one or more locking tabs 38 may be different) and the one or more gaps 40 may include variable arc lengths (e.g., the arc lengths Y of one or more gaps 40 may be different). Additionally, FIG. 6 illustrates that each locking tab 38 may include a length L, extending proximally from the second end 65 of the locking cap 32. In some examples, such as the example shown in FIG. 6, the length L of each locking tab 38 may be uniform, however, in other examples, the locking cap 32 may include locking tabs 38 having variable lengths L. In other words, in some examples, one or more of the locking tabs 38 may include tabs having variable lengths L.

As will be described in greater detail below, each of the locking tabs 38 may be designed to exert a force radially inward, toward the longitudinal axis 70. It can be appreciated that the thickness of each locking tab 38 may correspond the amount of radially force exerted by each individual locking tab 38. For example, increasing the thickness of locking tabs 38 may result in the locking tabs 38 being more resistant to flexing radially outward, and therefore, may exert increased forces radially inward.

However, each of the locking tabs 38 may also be designed such that they may flex radially outward such that they can be advanced over one or more portions of the first actuation coupling member 19 and/or the second actuation coupling member 20. The inward biasing force and the flexural capabilities of the locking cap 32 will be discussed in greater detail with respect to FIG. 8 below.

Figure 7:
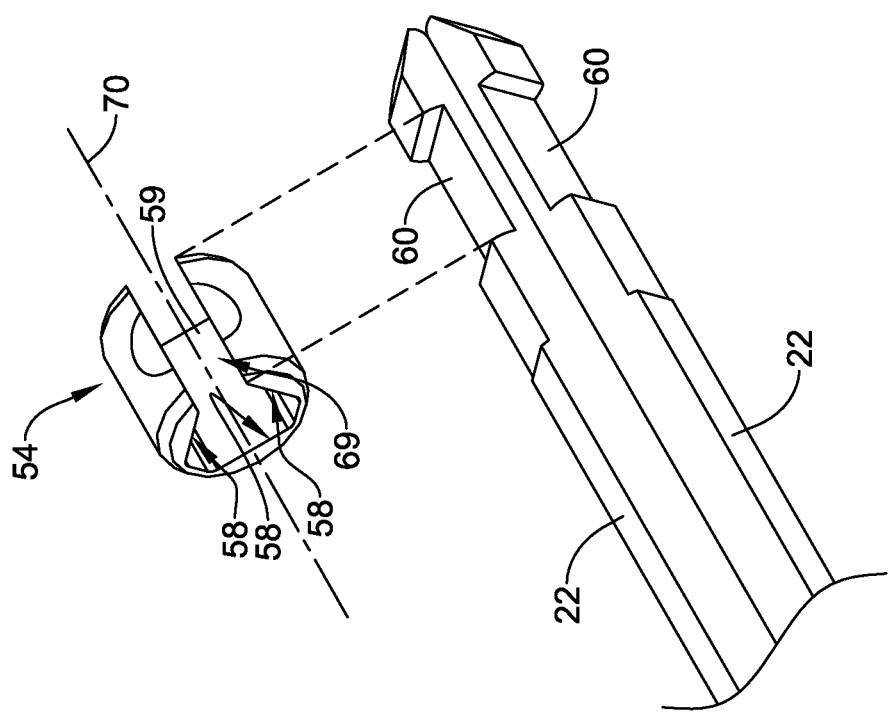
FIG. 7 is a perspective view showing multiple translation members and a securement collar of the connection assembly shown in FIGS. 3-4.

FIG. 7 illustrates a partial exploded view of the securement collar 54 spaced away from the distal end regions of the translation members 22. As shown in FIG. 7, the distal end region of each of the translation members 22 may include a notched portion 60. It can be appreciated from FIG. 7, that each of the notched portions 60 may be circumferentially offset from one another approximately 120 degrees. Additionally, FIG. 7 illustrates that the securement collar 54 may include an inner surface 59. Further, the inner surface 59 may include multiple flat surfaces 58, each of which may be offset 120 degrees from one another. It can be further appreciated that when the securement collar 54 is coupled to the translation members 22, each of the flat surfaces 58 may mate with each of the notched portion 60, respectively, of the securement collar 54.

It can be further appreciated that the securement collar 54 may include a gap 69 which prevents the securement collar 54 from extending continuously around its longitudinal axis 70 (it is noted that the securement collar 54 shares the same longitudinal axis 70 as the locking cap 32 described above). Therefore, the securement collar 54 may be designed to flex such that it may flex around and onto (e.g., it may snap onto) the translation members 22 (collectively) whereby each of the flat surfaces 58 engage each of the notched regions 60, respectively.

Figure 8:
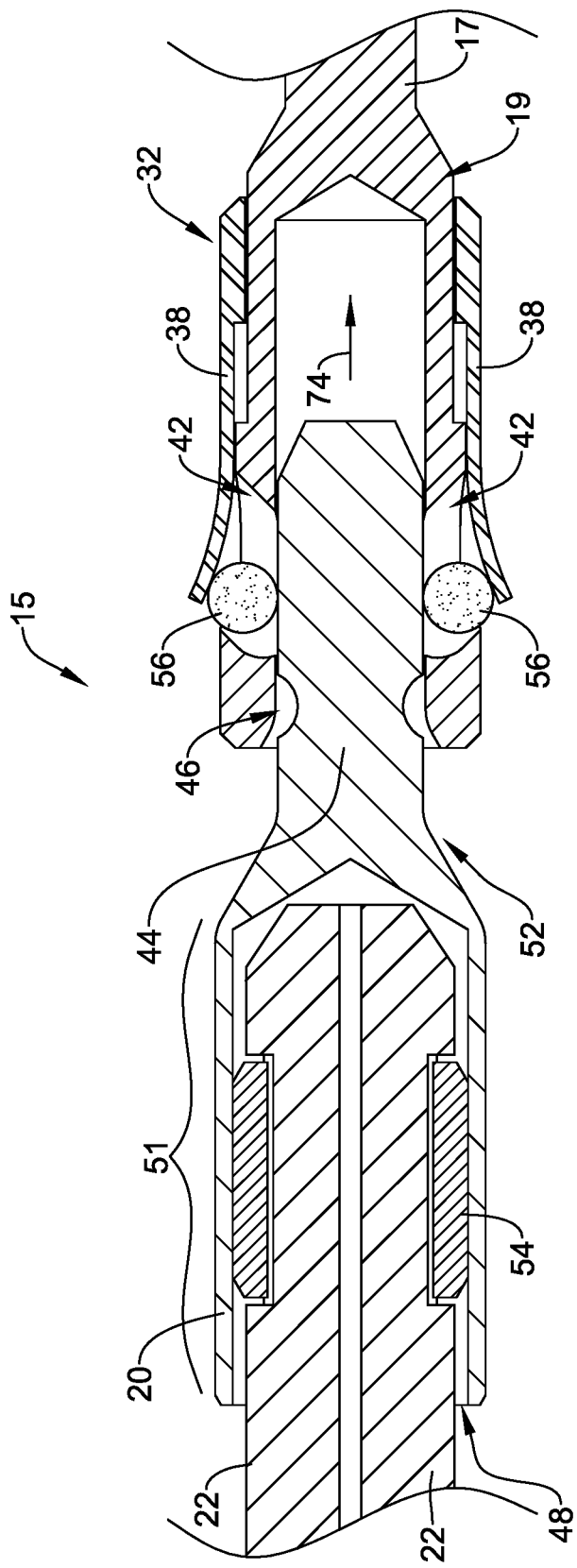
FIG. 8 is a cross-sectional view of the connection assembly in a disengaged configuration.

FIG. 8 illustrates a cross-sectional view of the stem 44 of the second actuation coupling member 20 being inserted into the lumen 52 (as depicted by the arrow 74) of the first actuation coupling member 19. FIG. 8 may be described as a "disengaged" configuration of the connection assembly 15 shown in FIG. 3 (e.g., disengaged prior to the connection assembly being fully engaged as shown in below in FIG. 9). It can be appreciated from FIG. 8 that as the stem 44 is inserted into the lumen 52, the portion of the outer surface of the stem 44 distal to the groove 46 may engage each of the spherical bearings 56, thereby pushing each of the spherical bearings 56 radially outward as the stem is advanced into the lumen 52. As each of the spherical bearings 56 is pushed radially outward, they may push against the locking tabs 38 of the locking collar 32 (which is positioned overtop a portion of the first actuation coupling member 19). However, FIG. 8 illustrates the locking tabs 38 of the locking cap 32 may be designed to flex radially outward while simultaneously maintaining an inward radially force such that each spherical bearing is permitted to shift radially outward to allow the stem 44 to be inserted into the lumen 52, but not to an extent in which the bearings 56 fall out of the apertures 42. It can be permitted that the spherical bearings 56 may remain in this position (and the locking tabs 38 may remain flexed) until the stem 44 is advanced to a positioned in which each of the bearings falls radially inward into the groove 46.

Figure 9:
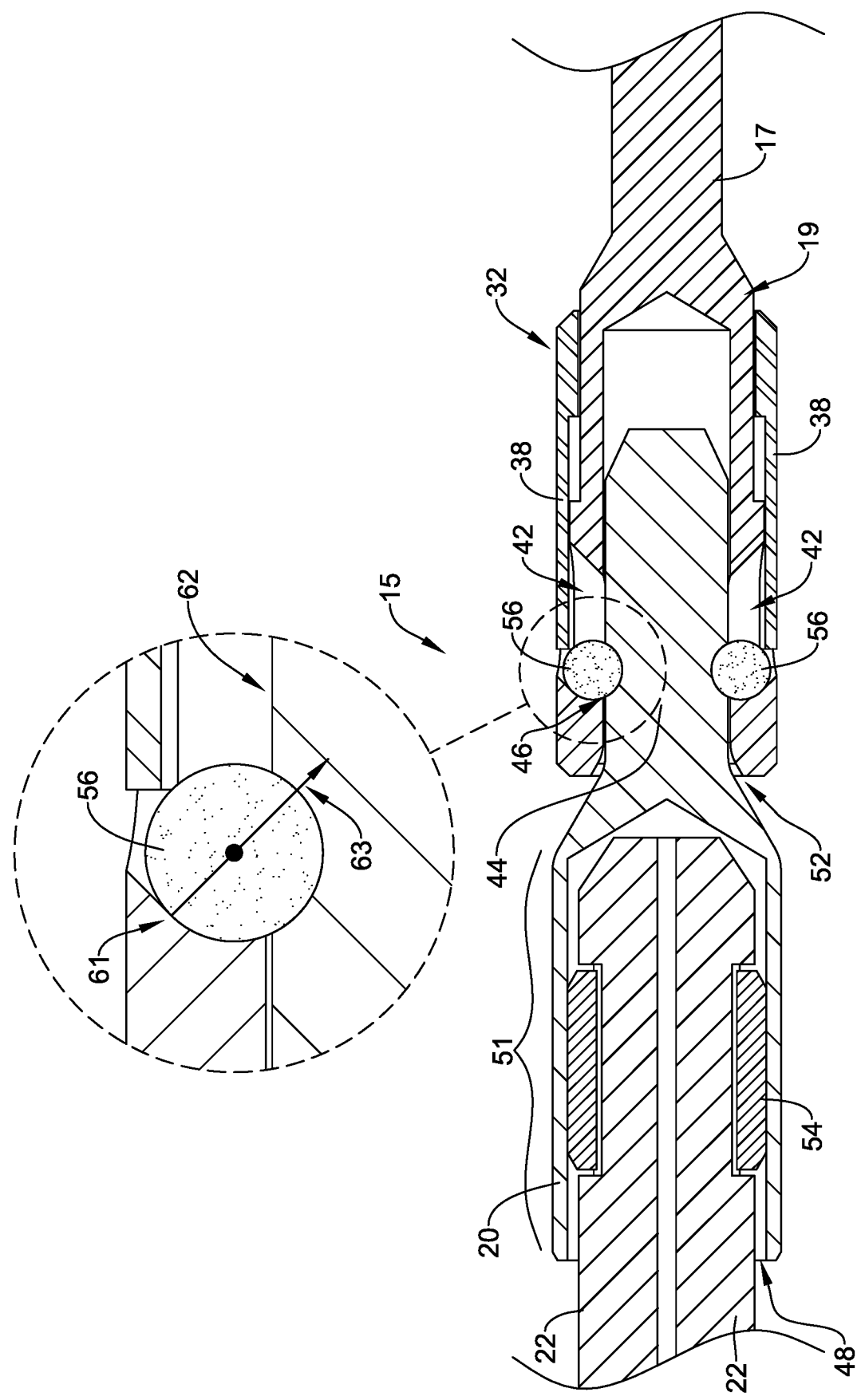
FIG. 9 is a cross-sectional view of the connection assembly in an engaged configuration.

FIG. 9 illustrates a cross-section of the connection assembly 15 shown in FIG. 8 after the spherical bearings 56 have been seated into the groove 46 (e.g., FIG. 9 illustrates the "engaged" configuration of the connection assembly 15). FIG. 9 may be described as an "engaged" configuration of the connection assembly 15 shown in FIG. 8. As described above, FIG. 9 illustrates two translation members 22 (it can be appreciated that the third translation member 22 is hidden behind the two visible translation members 22 shown in FIG. 7) inserted into the lumen 48 of the proximal end region 51 of the second actuation coupling member 20. Further, FIG. 9 illustrates the securement collar 54 positioned within the notched portions 60 of the translation members 22. As discussed above, the securement collar 54 may be welded directly to the second actuation coupling member 20.

FIG. 9 further illustrates the stem 44 of the second actuation coupling member 20 positioned within the lumen 52 of the first actuation coupling member 19. FIG. 9 further illustrates a portion of the spherical bearings 56 positioned within the groove 46 of the stem 44. FIG. 9 illustrates that the cross-sectional shape of the groove 46 may resemble a "half circle" having a radius of curvature which mirrors the radius of curvature of the groove 46.

As discussed above, each individual bearing 56 may rotate, slide, spin, translate, etc. around the circumference of the stem 44 while remaining within the groove 46. In other words, each of the bearings 56 is permitted to travel around the outer surface of the stem 44 within the groove 46, and each individual bearing 56 may be spinning, sliding, rotating, etc. while doing so. As described above, a portion of each individual spherical bearing 56 may be positioned in a single aperture 42, whereby the portion of the bearing 56 which extends radially outward of the groove 46 (e.g., the portion of the bearing which is not nested within the groove 46) may be positioned within the aperture 46. Additionally, as described above, FIG. 9 illustrates that locking tabs 38 of the locking collar positioned over top each of the spherical bearings 56, thereby preventing them from falling out of each of the apertures 42.

It can be further appreciated that when the bearings 56 are positioned within the groove 46, the locking cap 32 may be prevented from moving distally relative to the first actuation coupling member 19. In other words, the locking ca 32 may abut spherical bearings 56, which, in turn, abut the wall defining the aperture 42 of the first actuation coupling member 19.

Further, the engagement of each of the spherical bearings 56 with both a portion of the first actuation coupling member 19 (e.g., the bearings 56 engage the wall defining the aperture 42 of the first actuation coupling member 19) and a portion of the second actuation coupling member 20 (e.g., the bearings 56 are nested with the groove 46 of the stem 44 of the second actuation coupling member 20), prevents the first actuation coupling member 19 from being disengaged from the second actuation coupling member 20. In other words, after the stem 44 is inserted into the lumen 52 to a position in which the spherical bearings 56 fall into the groove 46, the stem 44 is prevented from being pulled out of the lumen 52.

Additionally, the detailed view of FIG. 9 illustrates the spherical bearing 56 resting within the groove 46 while also being positioned within a portion of the aperture 42. Additionally, the detailed view of FIG. 9 illustrates that, when the spherical bearing 56 is positioned within the aperture 42, the spherical bearing 56 may contact the angled surface of the aperture 42. Further, the detailed view illustrates a contact point 61 between the spherical bearing 56 and the angled surface of the aperture 42. The detailed view further illustrates an arrow 63 which represents a force vector extending from the contact point 61 and passes through the center of the spherical bearing 56. It can be appreciated that the angled surface of the aperture 42 must be great enough such that the force vector 63 passes below the outer surface 62 of the stem 44. It can be further appreciated that if the angled surface of the aperture 42 is not steep enough, the inward force imparted from the wall of the aperture 42 to the spherical bearing 56 and, subsequently to the groove 46, may not be great enough to prevent the spherical bearing 56 from being dislodged from the groove 46 under tensile loading conditions.

Additionally, it can be appreciated that when the spherical bearings 56 are nested within the groove 46, the second actuation coupling member 20 may be permitted swivel (e.g., spin along its longitudinal axis) relative to both the first locking actuation member 19 and the actuation shaft locking cap 32. Because the spherical bearings 56 may spin, rotate, etc. within the groove 46, the first actuation coupling member 19 may swivel relative to the second actuation coupling member 20.

Some example materials that can be used for the various components of the medical device system 10 are described herein. However, this is not intended to limit the devices and methods described herein, as the other materials may be utilized for the medical device system 10 and components thereof.

Additionally, medical device system 10 and components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylenc naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device system 10 and components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 and components thereof to achieve the same result.

In some embodiments, a degree of Magnetic Resonance Imaging (MRI) compatibility is imparted into the shaft. For example, the medical device system 10 and components thereof may include a material that does not substantially distort the image and create substantial artifacts (e.g., gaps in the image). Certain ferromagnetic materials, for example, may not be suitable because they may create artifacts in an MRI image. The medical device system 10 and components thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for delivering an implantable heart valve, comprising:
    a connection assembly having an engaged configuration and a disengaged configuration, the connection assembly including:
        an inner shaft having a proximal end region, a distal end region and a first coupling member disposed along a portion of the distal end region, wherein the first coupling member includes a plurality of apertures;
        a support shaft having a proximal end region, a distal end region and a second coupling member disposed along a portion of the proximal end region, wherein the second coupling member includes a stem, wherein the stem includes a groove extending circumferentially around the stem;
        a plurality of bearings, wherein each bearing is disposed in a respective aperture of the plurality of apertures, and wherein a portion of each bearing is also disposed in a portion of the groove when the connection assembly is in the engaged configuration; and
        a locking cap coupled to the inner shaft, wherein a portion of the locking cap is configured to cover at least a portion of each of the plurality of bearings when the connection assembly is in the engaged configuration.

2. The system of claim 1, wherein the locking cap includes a plurality of tabs extending circumferentially around a longitudinal axis of the locking cap.

3. The system of claim 2, wherein each of the plurality of tabs is configured to flex radially away from the longitudinal axis.

4. The system of claim 3, wherein each of the plurality of tabs is configured to flex radially away from the longitudinal axis as the stem in inserted into a lumen of the first coupling member.

5. The system of claim 4, wherein each of the plurality of tabs is configured to exert a radially inward force on each of the plurality of bearings in the engaged configuration.

6. The system of claim 5, wherein each of the plurality of bearings is configured to slide circumferentially around the stem while disposed within the groove.

7. The system of claim 6, wherein each of the bearings is configured to rotate relative to the first coupling member, the second coupling member and the locking cap in the engaged configuration.

8. The system of claim 7, wherein each of the bearings is configured to shift radially outward within its respective aperture of the plurality of apertures as the stem is inserted into a lumen of the first coupling member.

9. The system of claim 8, wherein each of the plurality of bearings is disposed within its respective aperture of the plurality of apertures in the disengaged configuration.

10. The system of claim 1, wherein the locking cap is fixedly attached to the first coupling member.

11. The system of claim 10, wherein the first coupling member is configured to rotate relative to the second coupling member in the engaged configuration.

12. A system for delivering an implantable heart valve, comprising:
 a tip assembly having a distal end region and a proximal end region;
 a guidewire shaft coupled to the distal end region of the tip assembly;
 a connection assembly having an engaged configuration and a disengaged configuration,
 the connection assembly including:
  an inner shaft having a proximal end region, a distal end region and a first coupling member disposed along a portion of the distal end region, wherein the first coupling member includes a plurality of apertures;
  a support shaft having a proximal end region, a distal end region and a second coupling member disposed along a portion of the proximal end region, wherein the second coupling member includes a stem, wherein the stem includes a groove extending circumferentially around the stem;
  a plurality of bearings, wherein each bearing is disposed in a respective aperture of the plurality of apertures, and wherein a portion of each bearing is also disposed in a portion of the groove when the connection assembly is in the engaged configuration; and
  a locking cap coupled to the inner shaft, wherein a portion of the locking cap is configured to cover at least a portion of each of the plurality of bearings when the connection assembly is in the engaged configuration.

13. The system of claim 12, wherein the locking cap includes a plurality of tabs extending circumferentially around a longitudinal axis of the locking cap.

14. The system of claim 13, wherein each of the plurality of tabs is configured to flex radially away from the longitudinal axis.

15. The system of claim 14, wherein each of the plurality of tabs is configured to flex radially away from the longitudinal axis as the stem is inserted into a lumen of the first coupling member.

16. The system of claim 15, wherein each of the plurality of tabs is configured to exert a radially inward force on each of the plurality of bearings in the engaged configuration.

17. The system of claim 16, wherein each of the plurality of bearings is configured to slide circumferentially around the stem while disposed within the groove.

18. The system of claim 17, wherein each of the bearings is configured to rotate relative to the first coupling member, the second coupling member and the locking cap in the engaged configuration.

19. The system of claim 18, wherein the first coupling member is configured to rotate relative to the second coupling member in the engaged configuration.

20. A method for delivering an implantable heart valve, the method comprising:
 attaching a first coupling member of an actuation shaft to a second coupling member of a support shaft of a medical device delivery system, the medical device delivery system including the implantable heart valve;
 wherein attaching the first coupling member of the actuation shaft to the second coupling member of the support shaft includes positioning a plurality of bearings into a groove of the second coupling member;
 advancing the medical device delivery system to a target site adjacent the heart; and
 deploying the implantable heart valve at the target site.

* * * * *